United States Patent [19]
Yorkey et al.

[11] Patent Number: 6,094,592
[45] Date of Patent: Jul. 25, 2000

[54] METHODS AND APPARATUS FOR ESTIMATING A PHYSIOLOGICAL PARAMETER USING TRANSFORMS

[75] Inventors: Thomas J. Yorkey, San Ramon; Paul D. Mannheimer, Danville, both of Calif.

[73] Assignee: Nellcor Puritan Bennett, Inc., Pleasanton, Calif.

[21] Appl. No.: 09/085,475

[22] Filed: May 26, 1998

[51] Int. Cl.[7] .................................................. A61B 5/00
[52] U.S. Cl. ................................................ 600/475; 600/310
[58] Field of Search ................................. 600/407, 310, 600/322, 323, 473, 475, 476; 356/41

[56] References Cited

U.S. PATENT DOCUMENTS

| | | | |
|---|---|---|---|
| Re. 35,122 | 12/1995 | Corenman et al. | 128/633 |
| 4,802,486 | 2/1989 | Goodman et al. | 128/633 |
| 4,869,254 | 9/1989 | Stone et al. | 128/633 |
| 4,911,167 | 3/1990 | Corenman et al. | 128/633 |
| 4,928,692 | 5/1990 | Goodman et al. | 128/633 |
| 4,934,372 | 6/1990 | Corenman et al. | 128/633 |
| 5,078,136 | 1/1992 | Stone et al. | 128/633 |
| 5,337,744 | 8/1994 | Branigan | 128/633 |
| 5,351,685 | 10/1994 | Potratz | 128/633 |
| 5,452,717 | 9/1995 | Branigan et al. | 128/633 |
| 5,482,036 | 1/1996 | Diab et al. | 128/633 |
| 5,490,505 | 2/1996 | Diab et al. | 128/633 |
| 5,632,272 | 5/1997 | Diab et al. | 128/633 |
| 5,645,060 | 7/1997 | Yorkey | 128/633 |
| 5,662,106 | 9/1997 | Swedlow et al. | 128/633 |
| 5,853,364 | 12/1998 | Baker, Jr. et al. | 600/300 |
| 5,857,462 | 1/1999 | Thomas et al. | 128/633 |
| 6,002,952 | 12/1999 | Diab et al. | 600/310 |

FOREIGN PATENT DOCUMENTS

WO 92/16142  10/1992  WIPO .............................. A61B 5/00

*Primary Examiner*—Marvin M. Lateef
*Assistant Examiner*—Shawna J Shaw
*Attorney, Agent, or Firm*—Beyer Weaver & Thomas LLP

[57] ABSTRACT

A method for use in a system for determining a physiological parameter is described. The system has a sensor for transmitting electromagnetic energy of first and second wavelengths toward a tissue sample and detecting the electromagnetic energy after scattering of the electromagnetic energy by the tissue sample, thereby generating a first signal corresponding to the first wavelength and a second signal corresponding to the second wavelength. The first and second signals are transformed into the frequency domain, thereby generating third and fourth signals. A ratio signal is generated using the third and fourth signals. For each of a plurality of ratio values an associated sum is generated corresponding to the number of times the ratio signal coincides with the ratio value associated with the sum. Contributions to each sum are weighted in accordance with the third signal. A best ratio value is selected from the plurality of ratio values based on the sums associated therewith.

32 Claims, 6 Drawing Sheets

METHODS AND APPARATUS FOR ESTIMATING A PHYSIOLOGICAL PARAMETER USING TRANSFORMS

BACKGROUND OF THE INVENTION

The present invention relates to methods and apparatus for estimating a physiological parameter using Fourier transforms. More specifically, the invention relates to a pulse oximetry system for estimating the oxygen saturation of hemoglobin in arterial blood in which a saturation value is determined from representations of the oximeter sensor signals in a transformed space.

Pulse oximeters measure and display various blood flow characteristics and blood constituents including but not limited to the oxygen saturation of hemoglobin in arterial blood. An oximeter sensor passes light through blood-perfused tissue and photoelectrically senses the absorption of the light by the tissue. The light passed through the tissue is selected to be of one or more wavelengths that are absorbed by the blood in an amount representative of the amount of the blood constituent being measured. The amount of light absorbed is then used to calculate the amount of the blood constituent present in the blood.

The sensed light signals can be degraded by both noise and motion artifact. One source of noise is ambient light that reaches the sensor's light detector. Another source of noise is electromagnetic coupling from other electronic instruments. Motion of the patient also introduces noise and affects the detected light energy. For example, the contact between the sensor's detector and/or emitter and the tissue sample can be temporarily disrupted when motion causes either to move away from the tissue. In addition, because blood is fluid, it responds differently than the surrounding tissue to inertial effects, thus resulting in momentary changes in volume at the point to which the oximeter sensor is attached. The degradation of the detected light energy can, in turn, result in degradation of the pulse oximeter output and inaccurate reporting of the blood constituent concentration. It will be understood that such inaccuracies can have negative consequences.

A variety of techniques have been developed to minimize the effects of noise and motion artifact in pulse oximetry systems. In a system described in U.S. Pat. No. 5,025,791, an accelerometer is used in the oximetry sensor to detect motion. When motion is detected, data taken during the motion are either eliminated or indicated as being corrupted. In U.S. Pat. No. 4,802,486, assigned to Nellcor Puritan Bennett, the assignee of the present invention, the entire disclosure of which is incorporated herein by reference, an EKG signal is monitored and correlated to the oximeter reading to provide synchronization to limit the effect of noise and motion artifact pulses on the oximeter readings. This reduces the chance of the oximeter locking onto a motion signal. In U.S. Pat. No. 5,078,136, assigned to Nellcor Puritan Bennett, the assignee of the present invention, the entire disclosure of which is incorporated herein by reference, signal processing techniques such as linear interpolation and rate of change analysis are employed to limit the effects of noise and motion artifact.

In another oximetry system described in U.S. Pat. No. 5,490,505, an adaptive noise canceler is used on different additive combinations of the red and infrared signals from the oximeter sensor to identify a coefficient for which the output of the noise canceler best represents the oxygen saturation of hemoglobin in the patient's blood. Unfortunately, this technique is computationally intensive resulting in an expensive implementation with undesirably high power requirements.

In yet another oximetry apparatus in U.S. Pat. No. 5,632,272, a technique using a Fourier transform is described. Data from the Fourier transform is analyzed to determine the arterial blood saturation, by considering all Fourier energies above a threshold with equal importance. However, the technique described in U.S. Pat. No. 5,632,272 is inadequate in the presence of significant random motion, where many anomalous signals exist above the noise threshold.

Because each of the above-described techniques has its own limitations and drawbacks, it is desirable to develop techniques for processing the signals from oximetry sensors to more accurately determine blood-oxygen levels in the presence of noise and motion artifact.

SUMMARY OF THE INVENTION

According to the present invention, a method and apparatus are provided by which noise from motion artifact and a variety of other sources is effectively removed from oximetry sensor signals for a reliable determination of the oxygen saturation of hemoglobin in a patient's arterial blood. Processed representations of the Red and IR signals from an oximetry sensor are combined in Fourier space and compared to a plurality of different values each of which corresponds to a different saturation value. A weighted count, also referred to herein as a sum, is maintained for each of the values which reflects the number of times the combined signal passes through the particular value. This information is used to generate a histogram or "saturation transform" of possible saturation values. The weights applied to contributions to each of the sums are selected in accordance with a representation of the IR signal in Fourier space. That is, individual contributions to each count are weighted according to the IR power level at the corresponding frequency.

The histogram typically includes a number of local maxima, only one of which corresponds to the arterial blood saturation value. According to various embodiments, selection of the appropriate maximum may be accomplished using any of a variety of peak selection algorithms. For example, according to one embodiment, the local maximum corresponding to the highest weighted count is selected. According to another embodiment, the local maximum corresponding to the highest saturation value is selected. According to yet another embodiment, the local maximum corresponding to a saturation value that is closest to the most recent motion-free saturation value is selected.

Thus, the present invention provides a method for use in a system for determining a physiological parameter. The system has a sensor for transmitting electromagnetic energy of first and second wavelengths toward a tissue sample and detecting the electromagnetic energy after scattering of the electromagnetic energy by the tissue sample, thereby generating a first signal corresponding to the first wavelength and a second signal corresponding to the second wavelength. The first and second signals are transformed into the frequency domain, thereby generating third and fourth signals. A ratio signal is generated using the third and fourth signals. For each of a plurality of ratio values an associated sum is generated corresponding to the number of times the ratio signal coincides with the ratio value associated with the sum. Contributions to each sum are weighted in accordance with the third signal. A best ratio value is selected from the plurality of ratio values based on the sums associated therewith.

A further understanding of the nature and advantages of the present invention may be realized by reference to the remaining portions of the specification and the drawings.

DESCRIPTION OF SPECIFIC EMBODIMENTS

Figure 1:
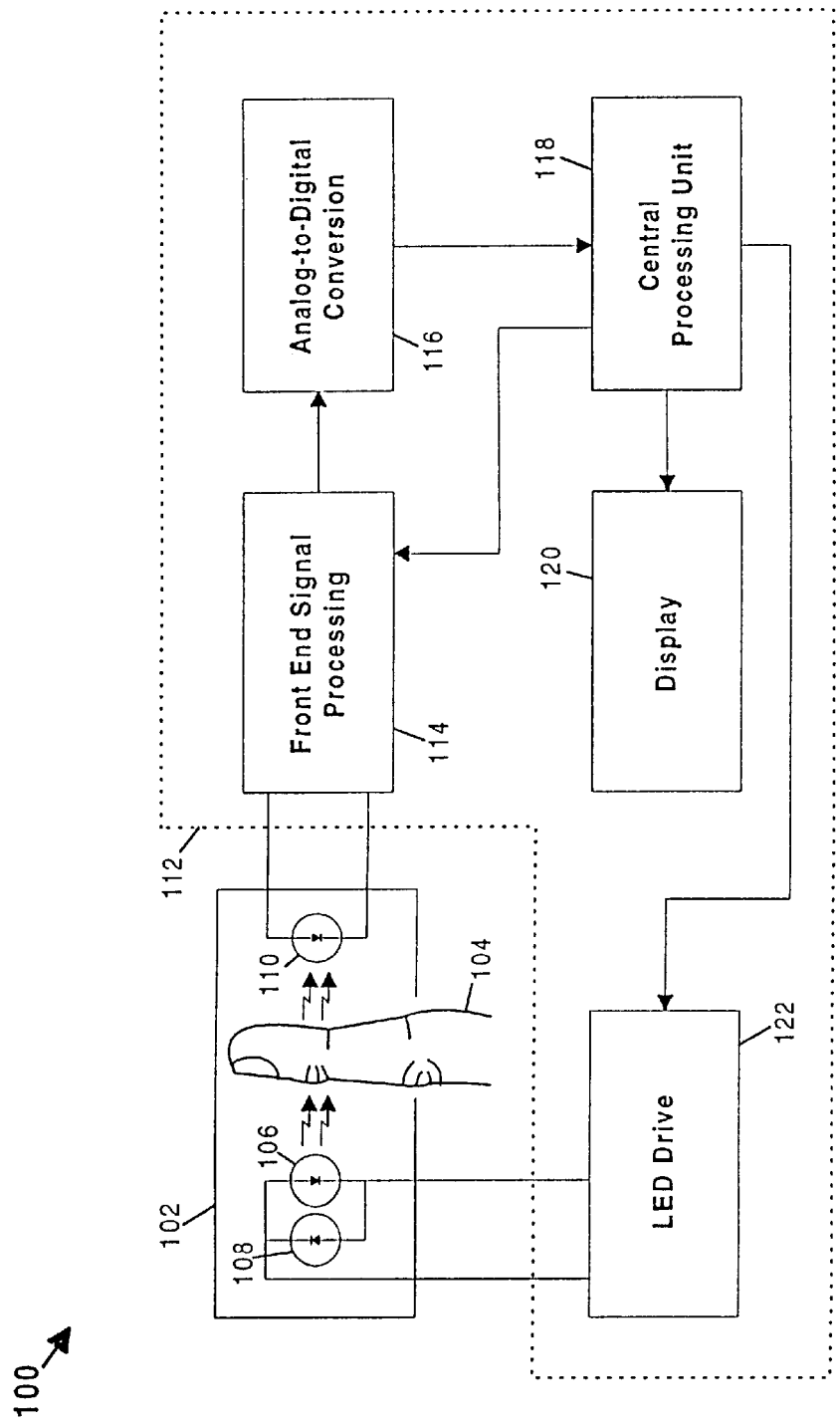
FIG. 1 is a block diagram of a pulse oximetry system for use with the present invention.

FIG. 1 is a block diagram of an oximetry system 100 for use with the present invention. An oximetry sensor 102 is attached to a blood perfused tissue sample such as a patient's finger 104. Red and infrared (IR) LEDs 106 and 108 alternately transmit Red and IR light toward finger 104. Detector 110 receives the Red and IR light transmitted through finger 104. Sensor 102 is connected to oximeter 112 which receives and processes the signal from detector 110, and which also provides the drive signal to LEDs 106 and 108. The detector signal is received by front end signal processing circuitry 114 which demodulates the alternately transmitted Red and IR light received by detector 110, cancels ambient light, and includes fixed and variable hardware gain stages prior to digitization.

The processed analog signal is converted to a digital signal by analog-to-digital conversion circuitry 116 and sent to central processing unit (CPU) 118 for computation of estimates of the oxygen saturation of hemoglobin in the patient's arterial blood according to a specific embodiment of the invention. The calculated saturation is then sent to display 120. CPU 118 also controls LED drive circuitry 122 which provides the drive signals for LEDs 106 and 108, and the demodulation of the collected light signals in front end circuitry 114. One example of an oximetry system for use with the present invention is described in commonly assigned, copending U.S. application Ser. No. 08/660,510 for METHOD AND APPARATUS FOR ESTIMATING PHYSIOLOGICAL PARAMETERS USING MODEL-BASED ADAPTIVE FILTERING filed on Jun. 7, 1996, which was based on Provisional Application Ser. No. 60/000,195 filed on Jun. 14, 1995, the entire specifications of which are incorporated herein by reference.

Figure 2:
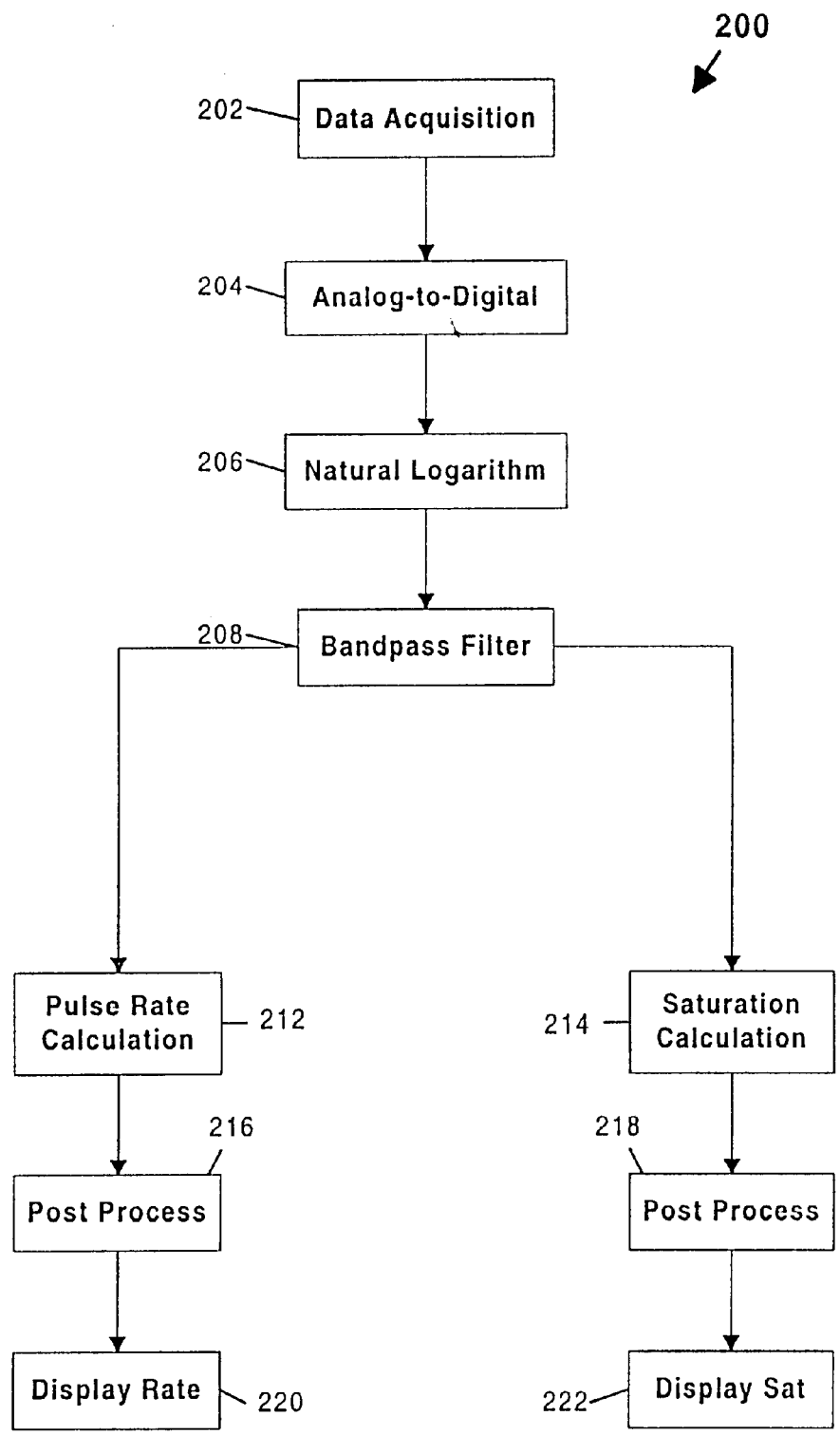
FIG. 2 is a flowchart illustrating the operation of the pulse oximetry system of FIG. 1.

FIG. 2 is a flowchart 200 illustrating the operation of the pulse oximetry system of FIG. 1. Data acquisition (step 202) may be achieved using a wide variety of available sensor and front-end analog signal processing such as, for example, sensor 102 and circuitry 114 of FIG. 1. The acquired data are digitized at an appropriate sample rate (step 204), and the natural logarithm of the digitized Red and IR waveforms is taken (step 206). The resulting data are then bandpass filtered (step 208) with an infinite impulse response filter (IIR) having a high pass cutoff at 0.5 Hz and a low pass roll off from 10 to 20 Hz.

The signals are then employed for calculation of the pulse rate and saturation (steps 212 and 214). The values yielded by these process steps are both subjected to post processing (steps 216 and 218) which uses available metrics with regard to the calculated values to determine their reliability and whether and how they should be displayed. The respective values are then displayed (steps 220 and 222). A portion of saturation algorithm 214 will now be described in greater detail with reference to FIG. 3.

Figure 3:
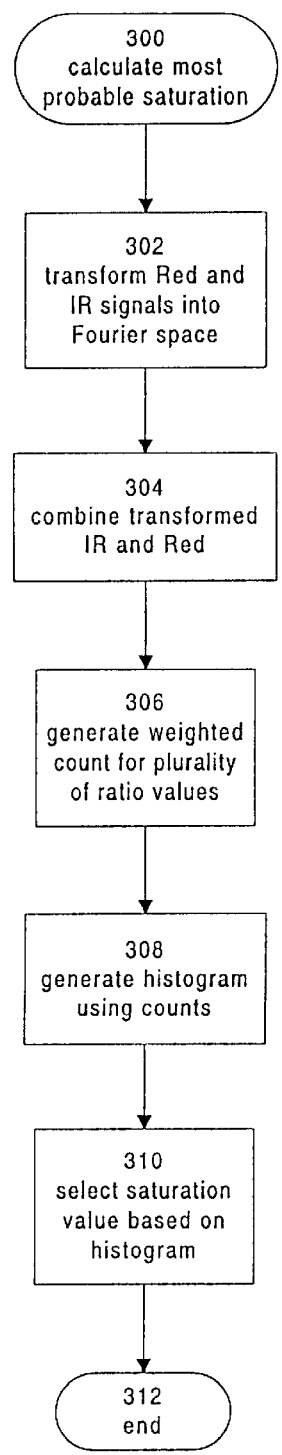
FIG. 3 is a flowchart illustrating the calculation of the oxygen saturation of hemoglobin in arterial blood according to a specific embodiment of the invention.
Figure 4A:
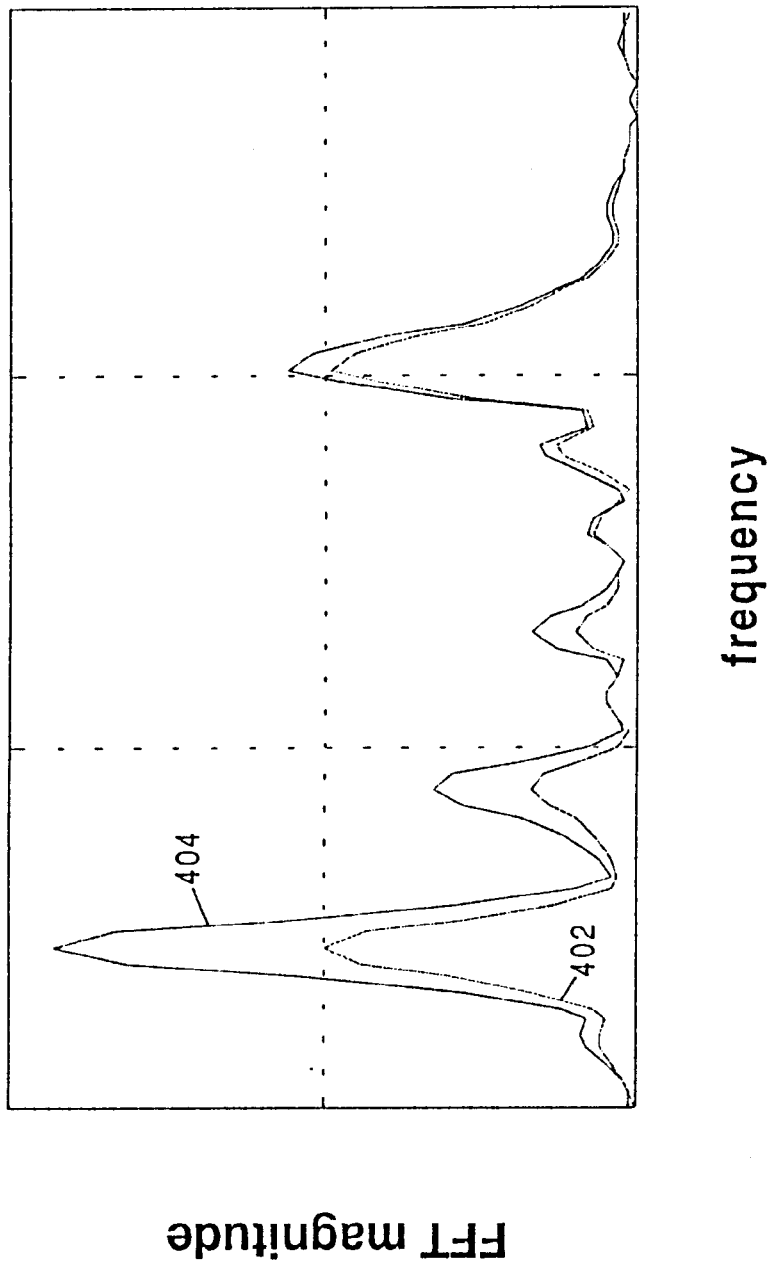
FIGS. 4a–4c are graphs showing representations of various signals used in the saturation calculation algorithm of the present invention.
Figure 4B:
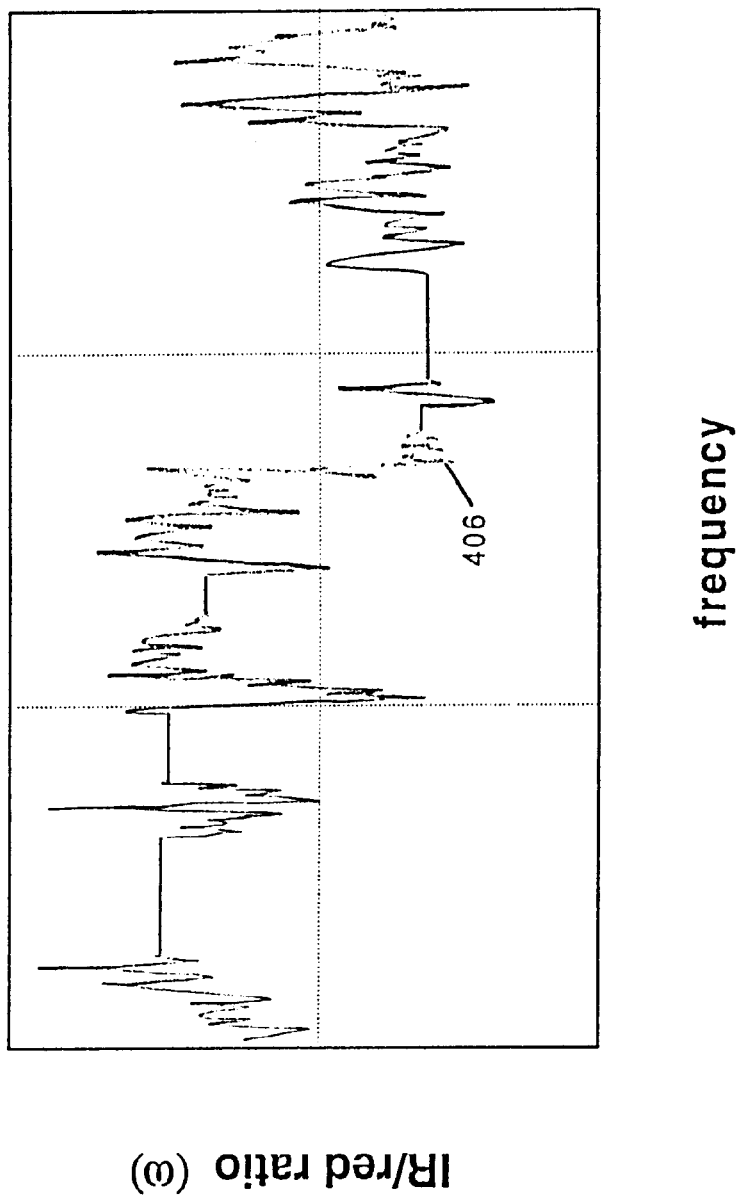
Figure 4C:
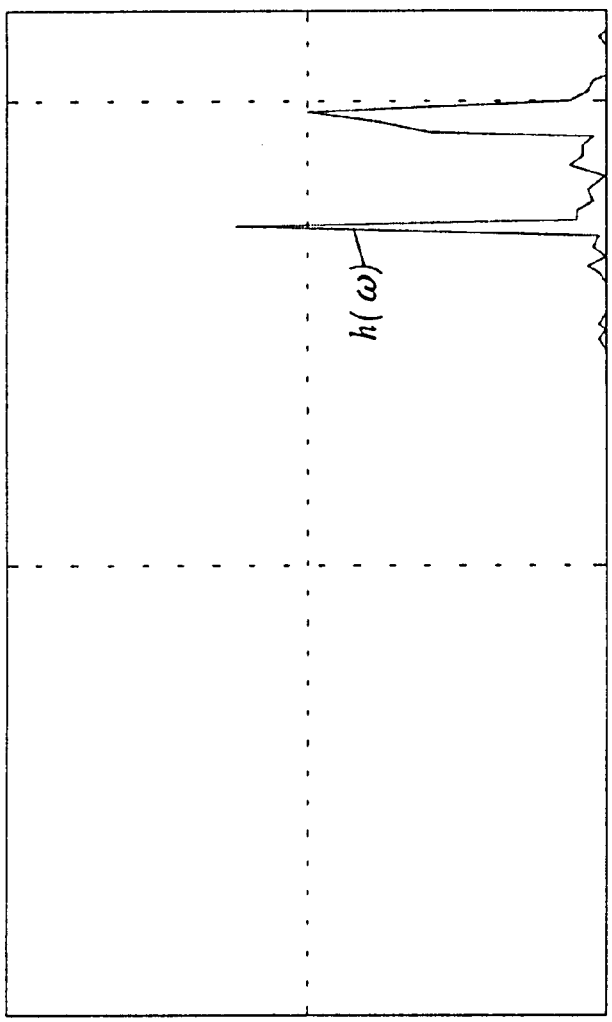

FIG. 3 is a flowchart 300 illustrating the calculation of the oxygen saturation of hemoglobin in arterial blood according to a specific embodiment of the invention. FIGS. 4a–4c show representations of various signals used in the saturation calculation algorithm of the present invention. It will be understood that the described embodiment may be used in conjunction with a plurality of other methods for calculating saturation to thereby provide several independently calculated values from which the best value may then be selected. According to a specific embodiment, the processed and digitized Red and IR signals are transformed into Fourier Space (step 302). This Fourier transform results in frequency samples $f_i$. The Fourier transformed signals are denoted by $IR(f_i)$ and $Red(f_i)$, which are both complex numbers. The relative magnitudes of some representative Fourier transformed signals are shown in FIG. 4a.

Both the Red and IR waveforms (402 and 404 respectively) have components at the heart rate (approximately 1 Hz) and multiples thereof. The IR signal is then combined with the Red signal (step 304) generating a ratio signal 406 (FIG. 4b) given by, $$\omega_i = \frac{Re\{IR(f_i)^* \times Red(f_i)\}}{IR(f_i)^* \times IR(f_i)}$$

Where * denotes a complex conjugate, and $Re\{x\}$ connotes the real part of $\{x\}$. As will be understood and as shown in FIG. 4b, ratio signal 406 is relatively stable in the frequency ranges around each multiple of the heart rate and apparently random outside of these ranges.

A weighted count or sum is then generated (step 306) for each of a plurality of ratio values, $\omega_i$. The counts represent the strength of the IR amplitude at frequency indices ($f_i$), where the ratio value $\omega_i$ equals the particular ratio value, $\omega$. That is $$h(\omega) = \sum_{\forall i \, s.t. \, \omega_i = \omega} |IR(f_i)|$$

Where the sum is for all i such that $\omega_i = \omega$.

The counts may be real numbers that correspond to the resolution of the measurement $|IR(f_i)|$, or may be integerized or quantized approximations. In a specific embodiment, more than two possible values of the counts/weights are used. A histogram is generated (step 308) using the counts for each $\omega_i$. An example of the histogram $h(\omega)$ is shown in FIG. 4c. According to a specific embodiment, the range of $\omega_i$ values is as follows:

$$0.4 < \omega_i < 2.5; \, \Delta\omega_i = 0.05$$

Each contribution to the count for a particular $\omega_i$ is weighted according to the strength of the IR signal at that Fourier index. That is, the weights accorded each transition of the ratio signal (FIG. 4b) through a particular ratio value $\omega_i$ are determined with reference to the amplitude of the IR signal as shown in FIG. 4a. Thus, the transitions that occur at or near the peaks (in Fourier space) of the IR waveform are weighted significantly more than those that occur where the IR amplitude is low. During motion, this typically results in a histogram having local maxima at two or more different values of $\omega_i$, only one of which corresponds to the actual saturation value.

If multiple peaks occur in the histogram, selection of the appropriate $\omega_i$ peak that corresponds to the arterial oxygen saturation for display (step 310) may be accomplished using a "peak selection" algorithm. Such an algorithm may be configured in a variety of ways including, but not limited to:
1) The peak with the largest weighted count may be selected;
2) The peak corresponding to the highest saturation value may be selected;
3) The peak corresponding to a saturation value that is closest to the most recent saturation value calculated prior to the onset of motion may be selected. According to one embodiment, determination of the presence of motion is accomplished with a "motion detection" algorithm such as disclosed in U.S. Pat. No. 5,662,106 for OXIMETER WITH MOTION DETECTION FOR ALARM MODIFICATION issued on Sep. 2, 1997, the entire specification of which is incorporated herein by reference for all purposes.
4) The peak corresponding to a saturation value closest to a predicted saturation value may be selected, where the predicted saturation value comes from following the trend of recently displayed saturations. According to various embodiments, this trend may, for example, incorporate the recently displayed saturation value, the time rate of change of recently displayed saturation values (i.e., saturation "velocity"), and the time rate of change of the change in recently displayed saturation values (i.e., saturation "acceleration") according to the following formula:

$$\text{predicted saturation} = \text{last displayed saturation} + C_v \cdot (dS/dt) + C_a \cdot (d^2S/dt^2),$$

where
$C_v$=velocity constant
$C_a$=acceleration constant
dS/dt=time rate of change of recent previously displayed saturations
$d^2S/dt^2$=time rate of change of recent values of dS/dt;
5) The peak corresponding to the higher of two tracking saturations may be selected, where trending (as described above) of each of the peaks present in the histogram is conducted and those which track one another may be associated with the venous and arterial blood oxygen saturations. That is, a pure "motion" peak often is created and is unchanging near $\omega_i=1$, while peaks that arise due to movement of venous and arterial blood will track one another, and in particular will track one another during a changing saturation condition. The $\omega_i$ peak corresponding to the higher saturation of the two "tracking" peaks is associated with the arterial oxygen saturation;
6) An algorithm that arbitrates between a subset of the algorithms listed above may be used, where arbitration is accomplished by choosing the most appropriate method to use based on various signal factors. Such signal factors may include, but are not limited to, the number of local maxima in the histogram, the absence or presence of motion, or the degree of motion. For example, according to a specific embodiment, in the absence of motion, method #2 is used. According to another embodiment, method #3 is used in the presence of motion. In another specific embodiment, the arbitrating algorithm is configured such that in the absence of motion and/or when two $\omega_i$ peaks are present, method #2 is used. However, if three or more peaks are present, method #5 is used.

Those skilled in the art will recognize that other schemes for selecting the $\omega_i$ peak corresponding to arterial saturation for display may be employed without departing from the scope of the invention.

While the invention has been particularly shown and described with reference to specific embodiments thereof, it will be understood by those skilled in the art that changes in the form and details of the disclosed embodiments may be made without departing from the spirit or scope of the invention. For example, signal transforms other than the Fourier transform may be employed. Other such transforms include the Wavelet Transform, the Cosine Transform, and the Legendre Polynomial Transform. Furthermore, more than two wavelengths of light could be utilized, such as described in commonly assigned U.S. Pat. No. 5,645,060 entitled METHOD AND APPARATUS FOR REMOVING ARTIFACT AND NOISE FROM PULSE OXIMETRY issued on Jul. 8, 1997, the entire specification of which is incorporated herein by reference for all purposes, or in the utilization of multivariate analysis in which many wavelengths are considered. Therefore, the scope of the invention should be determined with reference to the appended claims.

What is claimed is:

1. A method for use in a system for determining a physiological parameter, the system having a sensor for transmitting electromagnetic energy of first and second wavelengths toward a tissue sample and detecting the electromagnetic energy after scattering of the electromagnetic energy by the tissue sample, thereby generating a first signal corresponding to the first wavelength and a second signal corresponding to the second wavelength, the method comprising:

transforming the first and second signals into a frequency domain, thereby generating third and fourth signals;

generating a ratio signal using the third and fourth signals;

applying more than two variable weights to various parts of the ratio signal, the variable weights being derived with reference to at least one of the third and fourth signals;

for each of a plurality of ratio values in the ratio signal, generating an associated weighted sum corresponding to each time the ratio signal coincides with the ratio value associated with the sum; and selecting a best ratio value from the plurality of ratio values based on the sums associated therewith.

2. The method of claim 1 wherein the best ratio value corresponds to a most probable physiological parameter value.

3. The method of claim 1 wherein the more than two variable weights comprise a continuum of weights within a resolution of a measurement of the ratio signal.

4. The method of claim 1 wherein a number of the more than two variable weights exceeds a value from the group of $2^2$, $2^3$, $2^4$, $2^5$, $2^6$, $2^7$, $2_8$, $2_9$, $2_{10}$, $2^{11}$, and $2^{12}$.

5. The method of claim 1 wherein a histogram having a plurality of maxima represents all of the sums, one of the maxima corresponding to the best ratio value, and selecting the best ratio value comprises selecting the maximum corresponding to the best ratio value using a first peak selection algorithm.

6. The method of claim 5 wherein the first peak selection algorithm comprises identifying a maximum corresponding to a largest sum.

7. The method of claim 5 wherein the first peak selection algorithm comprises identifying a maximum corresponding to a highest value of the physiological parameter.

8. The method of claim 5 wherein the first peak selection algorithm comprises identifying a maximum corresponding to a physiological parameter value which is closest to a most recently reported value of the physiological parameter.

9. The method of claim 8 wherein the most recently reported value is calculated prior to an onset of motion.

10. The method of claim 9 further comprising detecting the motion.

11. The method of claim 5 wherein the first peak selection algorithm comprises identifying a maximum corresponding to a physiological parameter value which is closest to a predicted value of the physiological parameter.

12. The method of claim 11 wherein identifying the maximum comprises monitoring a trend in previously reported values of the physiological parameter.

13. The method of claim 12 wherein the trend is characterized by the time rate of change of the previously reported values of the physiological parameter.

14. The method of claim 12 wherein the trend is characterized by the time rate of change of the rate of change of the previously reported values of the physiological parameter.

15. The method of claim 5 wherein the first peak selection algorithm comprises identifying a first maximum which tracks at least one other maximum.

16. The method of claim 5 wherein the first peak selection algorithm is one of a plurality of peak selection algorithms, the method further comprising selecting the first peak selection algorithm from the plurality of peak selection algorithms based on at least one factor associated with the histogram.

17. The method of claim 16 wherein the at least one factor comprises a number of the maxima.

18. The method of claim 16 wherein the at least one factor comprises motion of the tissue sample.

19. The method of claim 1 wherein the electromagnetic energy comprises infrared and red radiation, the third signal corresponding to the infrared radiation and the fourth signal corresponding to the red radiation, the contributions to the sum associated with a particular ratio value being weighted according to the magnitude of the third signal.

20. The method of claim 1 wherein the physiological parameter comprises the blood oxygen saturation of hemoglobin in arterial blood, and each of the plurality of ratio values corresponds to a particular saturation value.

21. The method of claim 1 wherein transforming the first and second signals into the frequency domain comprises performing Fourier transforms on the first and second signals.

22. The method of claim 1 wherein each of the plurality of ratio values corresponds to a particular value of the blood oxygen saturation of hemoglobin in the tissue sample, a range of the ratio values being between 0.4 and 2.5, each of the plurality of ratio values being separated from adjacent ratio values by a first increment.

23. The method of claim 22 wherein the first increment comprises 0.05.

24. An apparatus for determining a physiological parameter, comprising:

a sensor for transmitting electromagnetic energy of first and second wavelengths toward a tissue sample and detecting the electromagnetic energy after scattering of the electromagnetic energy by the tissue sample, the sensor generating a first signal corresponding to the first wavelength and a second signal corresponding to the second wavelength; and a signal processor for calculating an estimate of the physiological parameter using the first and second signals, the signal processor having a central processing unit which is operable to transform the first and second signals into a frequency domain, and thereby generate third and fourth signals;

generate a ratio signal using the third and fourth signals;

apply more than two variable weights to various parts of the ratio signal, the variable weights being derived with reference to at least one of the third and fourth signals;

for each of a plurality of ratio values in the ratio signal, generate an associated weighted sum corresponding to each time the ratio signal coincides with the ratio value associated with the sum; and select a best ratio value from the plurality of ratio values based on the sums associated therewith.

25. A method of estimating a physiological variable of living tissue, comprising:

detecting at least first and second time domain signals corresponding to at least two light wavelengths scattered by living tissue;

transforming the time domain signals into another domain and associated other domain signals;

using the other domain signals to calculate a plurality of values representative of the physiological variable at a like plurality of different other domain signals;

applying more than two variable weights to various ones of the values to form weighted values, the variable weights being derived with reference to at least one of the other domain signals; and compiling the weighted values to estimate the physiological variable.

26. The method of claim 25 wherein the other domain is a frequency domain.

27. The method of claim 26 wherein each of the plurality of values comprises a ratio between first and second frequency domain signals at a common frequency corresponding to the value.

28. The method of claim 26 further comprising detecting a heart rate from at least one of the frequency domain signals.

29. The method of claim 26 wherein the variable weights are determined with reference to an energy level associated with each of the frequency domain signals.

30. The method of claim 25 wherein transforming the time domain signals comprises performing one of a Fourier transform, a Laplace transform, a Wavelet transform, a cosine transform, a Bessel transform, and a Legendé polynomial transform.

31. The method of claim 25 wherein the variable weights correspond to at least two bits of binary weighting resolution.

32. The method of claim 25 wherein the physiological variable comprises arterial oxygen saturation.

* * * * *